United States Patent [19]

Wortrich

[11] Patent Number: 4,963,131
[45] Date of Patent: Oct. 16, 1990

[54] DISPOSABLE CASSETTE FOR OPHTHALMIC SURGERY APPLICATIONS

[75] Inventor: Theodore S. Wortrich, Long Beach, Calif.

[73] Assignee: Surgin Surgical Instrumentation, Inc., Placentia, Calif.

[21] Appl. No.: 324,018

[22] Filed: Mar. 16, 1989

[51] Int. Cl.[5] ............................................. A61M 1/00
[52] U.S. Cl. ..................................... 604/34; 604/250; 604/33
[58] Field of Search ................................. 604/30–34, 604/250; 417/360

[56] References Cited

U.S. PATENT DOCUMENTS 4,457,699  7/1984  Hattori .................................. 251/7
4,559,036  12/1985  Wunsch ............................... 604/250
4,713,051  12/1987  Steppe et al. ......................... 604/34
4,725,269  2/1988  Danby et al. ......................... 604/250

Primary Examiner—Stephen C. Pellegrino
Attorney, Agent, or Firm—Merchant, Gould, Smith, Edell, Welter & Schmidt

[57] ABSTRACT

A superior cassette is provided for maintaining sterility of internal tubing sections that are to be repeatedly clamped under the control of external actuators when the cassette is inserted in an associated system, such as an irrigation/aspiration system for ophthalmic surgery applications. An inserted leading edge presents faces of interior sliders to actuators which reciprocate the slider to engage and clamp tubing sections positioned near the opposite, intercoupling edge of the cassette. All contact is made within the sterile interior of the cassette so that sterile flows cannot be contaminated even if leakage or puncture occurs under handling or repeated operation.

13 Claims, 3 Drawing Sheets

DISPOSABLE CASSETTE FOR OPHTHALMIC SURGERY APPLICATIONS

BACKGROUND OF THE INVENTION

This invention relates to disposable cassettes for transporting sterile solutions, and more particularly to such cassettes for use in irrigation and aspiration systems for ophthalmic applications.

Much equipment used in surgical procedures now utilizes disposable units wherever this is economically feasible. Experiences with contamination of reused units and components, together with the availability of low cost but high performance moldable materials, have resulted in this trend. Consequently, where a sterile fluid or material is to be passed to a surgical site, or various sterile flows are to be combined, systems are designed so that each surgical procedure is carried out using a new tubing set. Further benefits are derived with these systems from the fact that peristaltic pumps, using movable rollers, can operate directly on the tubing exterior to advance the fluid, or conversely, to block flow in a tubing simply by externally pinching the tubing. Neither event affects the sterility of the internal tubing in ordinary operation.

In typical practice, presterilized disposable tubing sets are configured for particular applications, sometimes including small disposable accessories as well. Before use, the operator removes the tubing set from a sterile container or package and, under sterile conditions, makes the necessary attachments from point to point. It was evident, quite early in the usage of such sets, that some convenience and other advantages could be gained by incorporating the tubing in a cassette, arranged so as to eliminate the necessity for threading tubing through the operative parts of a machine. There are numerous examples of such disposable cassettes, including a number of tubing cassettes for use with peristaltic pumps. In exchange for the ease of installation, and the reduction in chance of operator error, disadvantages are presented in terms-of cost, the need in some instances for complex internal tubing paths that may involve sharp bends, and often the unsuitability of the cassette in the event of any modification, however minor, of the operative parts of the system.

A specific example of the problems involved is evidenced by U.S. Pat. No. 4,713,051 to Steppe et al. This unit is intended for usage with an irrigation/aspiration system for ophthalmic microsurgery. A sterile solution is fed via irrigation tubing through the top of a cassette housing, and around an element providing a backup surface or boss adjacent an opening in the leading edge of the cassette, which is inserted into the machine in edgewise fashion. A clamp is engageable against the tubing and the boss, to pinch the tubing and stop the passage of sterile solution out a side edge of the cassette toward a handpiece. Controls available to the surgeon enable aspiration of non-sterile fluid and tissue from the surgical site back through an aspiration line into a side edge of the cassette and out to an attached waste bag. A length of the tubing close to the front edge of the cassette is exposed adjacent a semicircular surface against which a peristaltic pump may be engaged so as to withdraw the aspiration fluid. A shunt line from the aspiration line, within the cassette, leads to a vacuum control system opening at the front edge, into which an occluder shaft fits so as to control the differential pressure level available in the aspiration manifold. By operating the controls, the surgeon or technician can open the shunt line to provide instant backflow of irrigation fluid so that cortical material that is caught in the handpiece can be immediately cleaned out.

The system shown in U.S. Pat. No. 4,713,051 has a number of practical disadvantages. The element or member which controls irrigation flow by pinching the irrigation line is a non-sterile member, and must be operated many times in the course of a surgical procedure. In the event of puncturing or fracturing the irrigation line, the result is exposure of the sterile irrigation fluid to contaminants. While leakage external to the cassette might be visible to the operator, leakage arising in the interior of the installed cassette cannot be observed, so that contamination would be carried to the surgical site. Another disadvantage is that the tubings, as mentioned, enter or exit from three different sides of the cassette, making the unit unwieldy to handle. In addition, the internal configuration involves sharp bends in the tubing which can give rise to kinking and substantial impedance to flow. The tubing sections can also shift and even come loose in this configuration and the length of the tubing involved necessitates priming with an excessive amount of sterile solution. Further, the attached bag is internally secured and cannot be changed except by replacing the entire cassette. In the event of a long surgical procedure, therefore, as the bag capacity is approached the only feasible expedient is cassette replacement.

As noted above, such a unit does not permit any degree of variation in the design of the system which is to receive it. Even changes of tubing sizes can result in outmoding of the particular cassette design. In point of fact, the design shown in the patent was outmoded by a change in the configuration of the system, known as the CooperVision 10,000, to incorporate a separate pinch valve based upon an earlier design, the CooperVision "KCP" machine. In the original 10,000 model, when a surgeon desired to terminate aspiration immediately, he placed the pedal control in position to operate the vacuum control system so as to break the suction. The modified system incorporated a feature of the KCP machine using a shunt between the incoming irrigation line and the vacuum control system (VCS) line, this shunt line being normally closed by a pinch valve. Opening the shunt pinch valve at the same time as aspiration suction is reduced provides a separate path for flow of irrigation solution into the aspiration line going to the handpiece. This positive backflow, referred to as "venting", is instantly provided to the operative site through the aspiration line to enable clearing the handpiece. This relatively modest change in the configuration of the system to employ a conventional feature necessitated a new cassette and substantially increased the difficulties mentioned as to the configuration of U.S. Pat. No. 4,713,051.

Another difficulty encountered with this system has not been resolved since the introduction of the shunt line. The internal tubing sections being relatively long, mechanical resonances appear as suction is applied during the delicate phase of aspirating while the surgeon is working within the capsule of the lens. The resonance in the system is transmitted during aspiration at the aspiration part of the handpiece and is not only disturbing to the surgeon but introduces unnecessary risk factors when working within the capsule.

SUMMARY OF THE INVENTION

An end loaded tubing cassette has a leading edge structure that includes operative couplings for a peristaltic pump, an irrigation clamp, a shunt flow clamp and a vacuum control system opening. The cassette is provided with an intercoupling side opposite the leading edge side, with the internal tubing being principally disposed proximate the intercoupling side, except for a non-sterile aspiration tubing section that passes adjacent the peristaltic pump opening. Sliders engaged in openings in one broad wall of the cassette housing are exposed to the control elements in the machine when the cassette is inserted and span the housing interior to the relevant tubing sections. The sliders include operative ends extending toward the intercoupling side, spaced apart from fixed reference surfaces toward which they are directed, with the different irrigation and shunt tubing sections being disposed therebetween. The sliders form part of the internal sterile mechanism of the cassette, and in the event of fracturing or penetration of the tubing internally to the cassette, the sterile contents do not come into contact with contaminating sources. In addition, the shunt tubing connection intercommunicating with the vent line and the peristaltic pump is not only relatively short but is clamped in this geometry at a point close to the vent line. Only a very short segment of tubing thus is subjected to the drop in pressure and line resonances are not introduced.

This arrangement permits usage of the same basic construction to accommodate dimensional and some positional variations in tubing or exterior mechanism. Moreover, the tubing is all held at the intercoupling edge by a stabilizer bar insertable in a section of the cassette housing. The stabilizer bar provides a secure retainer for the tubing ends, to assure against slippage and misplacement. This configuration also minimizes the internal length of tubing needed, reducing by a substantial amount the priming volume required. Further, in accordance with the invention, the unit incorporates means for supporting a replaceable bag into which the aspirated tissue and fluids are passed, and which may be interchanged in the event that capacity is approached during a surgical procedure.

BRIEF DESCRIPTION OF THE DRAWINGS

A better understanding of the invention may be had by reference to the following description, taken in conjunction with the accompanying drawings, in which.

DETAILED DESCRIPTION OF THE INVENTION

Figure 1:
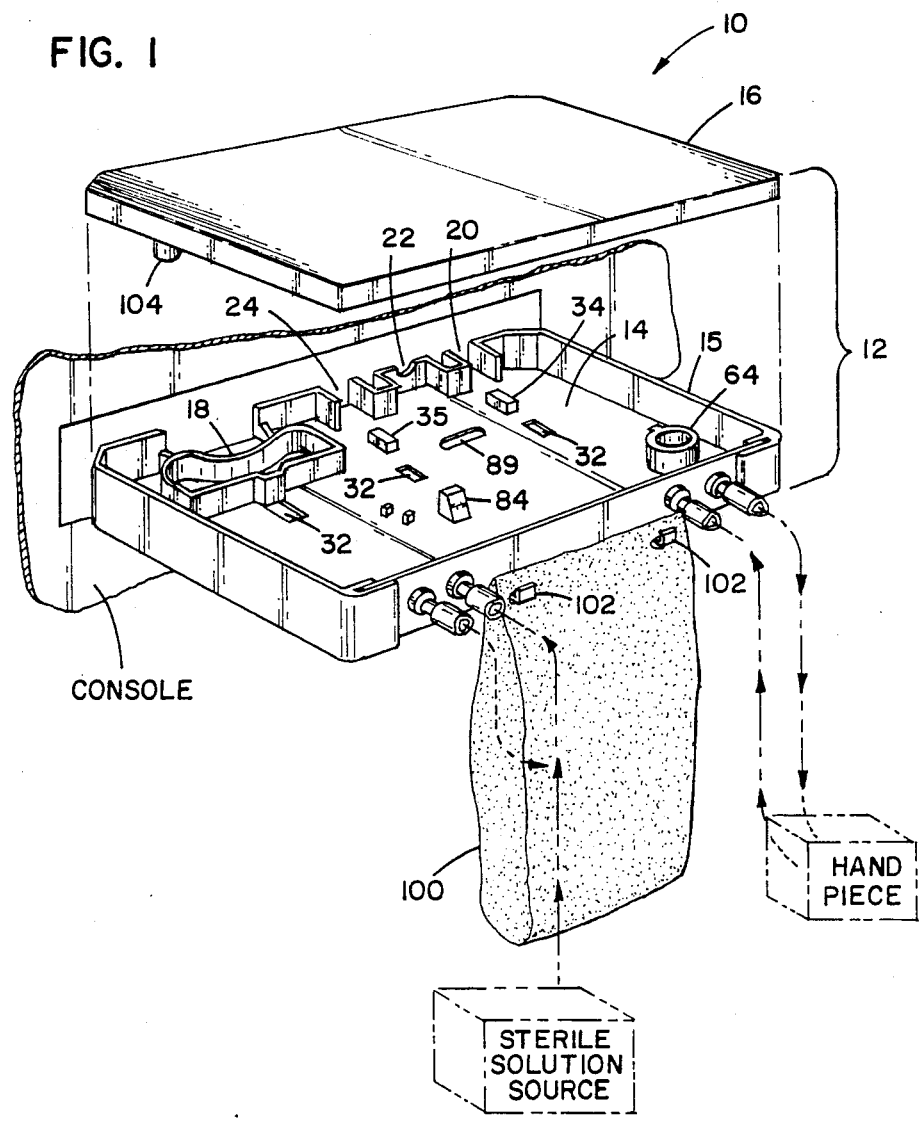
FIG. 1 is an exploded, perspective, view of a disposable cassette in accordance with the invention.
Figure 2:
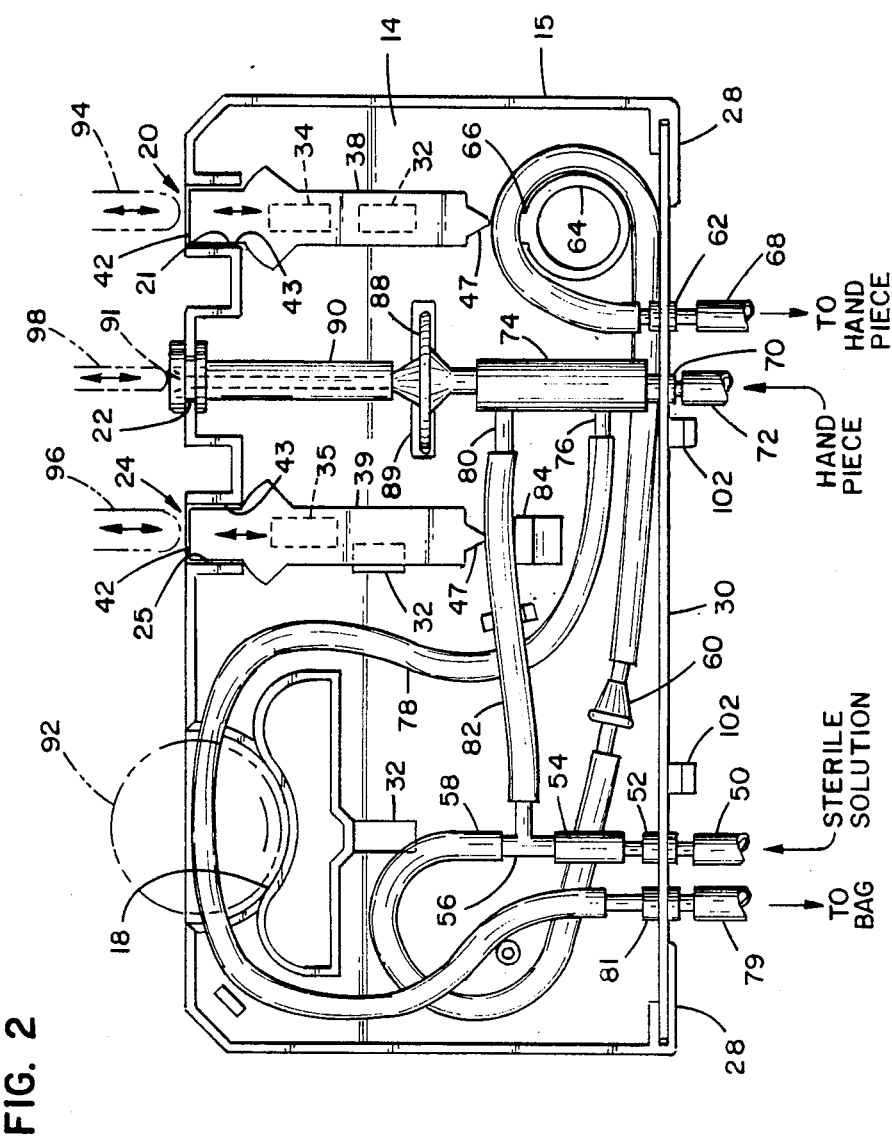
FIG. 2 is a plan view of a base section of the cassette of FIG. 1, showing the tubing in place.
Figure 3:
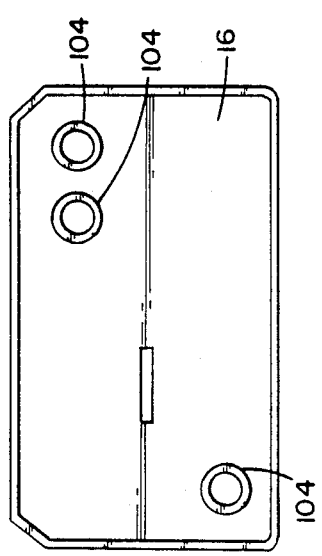
FIG. 3 is a plan view of a top section of the cassette of FIG. 1, without tubing.

A cassette 10 in accordance with the invention, referring now to FIGS. 1-3, comprises a housing 12 defining a split body including a base 14 having a side edge 15 around its periphery and matching with a top section 16 to define a rectangular configuration with a substantially hollow interior. The housing 12 has a leading edge for insertion into a receiving system console, the leading edge including a semicircular aspiration boss 18 into which a peristaltic roller (not shown in detail) is to be engaged when the cassette 10 is fully inserted. The leading edge also includes an irrigation control slot 20 defined by spaced apart side walls 21, a vacuum control system opening 22 and a shunt control slot 24 defined by short side walls 25. The shunt control slot 24 is closest to the aspiration pump boss 18, with the irrigation control slot 20 being furthest and the vacuum control system opening 22 being intermediate the two slots. The opposite longitudinal edge of the housing 12, in the base 14, defines what may be called an intercoupling edge having end tabs 28 defining receiving apertures for a stabilizer bar 30 that extends substantially the length of the intercoupling edge, which is exposed or accessible when the cassette 10 is inserted. The broad wall of the housing base 14 includes three spaced apart latch openings 32 which are engaged by the associated mechanism to hold the cassette 10 in the fully inserted position against the pressure of the actuating devices.

Figure 4:
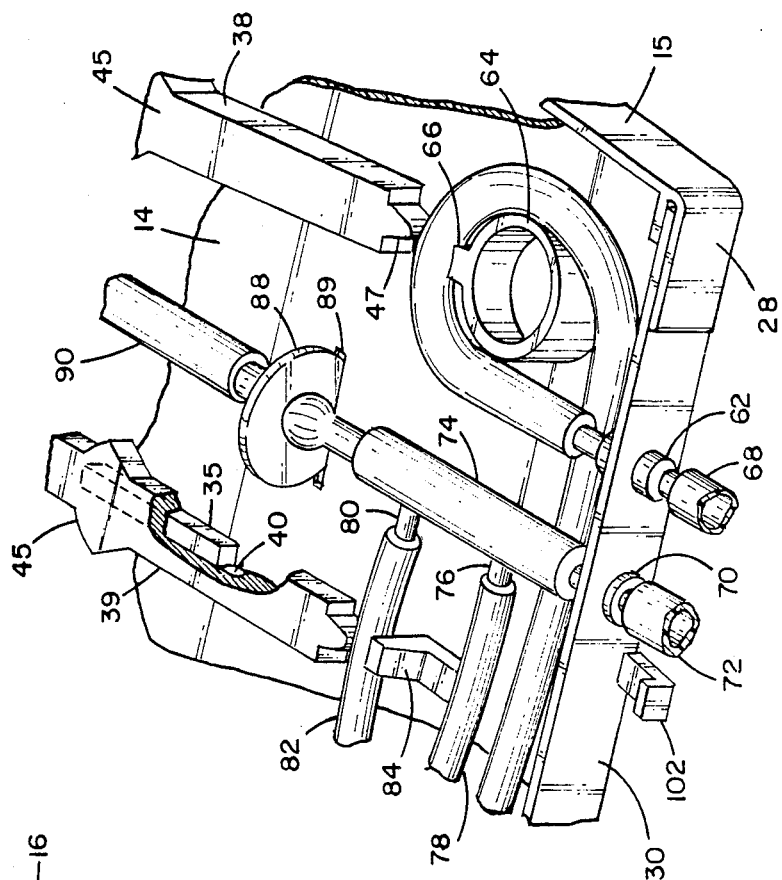
FIG. 4 is a fragmentary perspective view, partially broken away, of the arrangement of FIG. 1, showing the manner in which the sliders fit within the housing, and the stabilizer bar is mounted in a portion of the housing.

As best seen in FIG. 4, to which reference should also be made, the broad wall of the housing base 14 also includes a pair of spaced apart slider tongues 34, 35 in front to back separate alignment with the irrigation control slot 20 and the shunt slot 24, respectively. On these tongues 34, 35 are slidably mounted individual slider bars 38, 39 respectively, which as seen in FIG. 4 include an underside groove 40 for receiving the underlying tongue 34 or 35 respectively. The slider bars 38, 39 include an exposed end face 42 and adjacent side guide walls 43, the side walls 43 mating in slidable fashion within the side walls 21 or 25 adjacent the associated slot 20 or 21. Short wings 45 on each side of the slider bars 38, 39 limit outward movement by engagement against the side walls 21 or 25. At the opposite, interior, end of the slider bars 38, 39 are included small projections 47 for engaging an associated tubing section. The shapes of these projections 47 can be matched to the type of tubing material and are not dependent on the designs of the actuators in the system. The length of a slider bar 38 or 39 can also be varied if it is desired to make a change in the size or character of the tubing.

The irrigation line 50 from the system (not shown) provides sterile irrigation fluid under pressure, as from a drip chamber (not shown) at a selected height. The line 50 is coupled to an irrigation inlet fitting 52 seated in the stabilizer bar 30, to which a short length of intermediate tubing section 54 provides a coupling via the in-line end of a T-fitting 56 to a length of irrigation tubing 58 that is curved toward an irrigation outlet point adjacent the opposite side of the housing 12. In a mid-region of this irrigation line 58 is a one-way valve 60 that blocks reverse passage of fluid in the direction toward the sterile source. Adjacent an irrigation outlet fitting 62, the irrigation tubing 58 encircles a fixed guide 64 having a shaped abutment surface 66, against which the projection 47 on the adjacent slider bar 38 can press the irrigation tubing 58 to pinch it down. The outlet fitting 62 is connected to an irrigation handpiece line 68 of substantial length leading to the handpiece at the surgical site.

Adjacent the irrigation outlet fitting 62 is an aspiration return fitting 70 to which an aspiration handpiece line 72 is coupled. Interior to the housing 12, a double-T fitting 74 includes a first T branch 76 which is coupled to an internal aspiration tubing section 78 that leads in a curved path past the aspiration pump boss 18. The aspiration tubing section 78 passes out to a waste line 79 via a fitting 81 in the stabilizer bar 30. The second T branch 80 of the fitting 74 is coupled to a shunt tubing section 82 that is connected to the perpendicular branch arm of the T-fitting 56. The shunt tubing section 82 is relatively short and passes between the projection 47 on the end of the slider bar 39 and a stop block 84 that provides a fixed reference against which the slider bar 39 can pinch the shunt tubing section 82. The clamping action is exerted in this example about one inch away from the fitting 74 in a practical exemplification of the system. The in-line outlet of the double-T fitting 74 is coupled to a bacterial filter disk 88, the edge of which fits into an opening 89 in the base 14. The filter 88 in turn is coupled to a VCS grommet 90, the exterior end of which is seated in the VCS opening 22 and the center of which is open. An aperture 91 in the end of the VCS grommet 90 seats to the vacuum control system of the unit, which limits the vacuum level attainable in the aspiration line 72, thus controlling the aspiration suction exerted on tissue and fluid when the cassette is seated in place.

When the unit is inserted in a control console, leading edge first, the leading edge surfaces of the elements in the cassette 10 are as shown in FIG. 2 relative to the control elements operated by the console. A peristaltic pump roller 92 (FIG. 2 only) engages the aspiration tubing section 78, forcing it against the semicircular aspiration boss 18. An irrigation actuator 94 opposes the end surface of the slider bar 38, while a shunt actuator 96 opposes the end surface of the slider bar 39. Intermediate these two bars 38, 39, a VCS fitting 98 from the console establishes communication with the aperture 91 in the center of the VCS grommet 90.

At the intercoupling edge of the cassette 10 a bag 100 is replaceably hung on extending hooks 102, as seen in FIG. 1, although snap fasteners or other disengageable means may be used. The top section 16 of the cassette 10 fits in complementary fashion to the larger bottom unit, and (referring to FIG. 3) includes guides 104 for mating within apertures in the pump boss 18 and the guide 64 to secure the two parts of the housing in alignment.

In operation of the system of FIGS. 1-4, the cassette 10 having been inserted fully into the receiving slot in the console, latches (not shown) engage the latch openings 32 in the bottom side wall, holding the cassette 10 in position. In this position, the pump roller 92 is constantly engaged with the aspiration tubing section 78, although not necessarily rotating. When the operating process takes place, irrigation flow alone can be used. In this mode the irrigation actuator 94 is held out of contact with the slider bar 38, so that sterile solution under pressure passes from the irrigation line 50, through the inlet fitting 52, and through the one-way valve 60 to the irrigation handpiece line 68. The shunt actuator 96, however, is activated, forcing the second slider bar 39 down onto the shunt tubing section 82, blocking sterile solution from the second T branch 80. In another mode, aspiration and irrigation are concurrent, as determined by the surgeon using the appropriate control (foot pedal in most instances). Tissue and fluid from the surgical site are returned through the aspiration tubing section 72 to the double-T fitting 74, and then to the aspiration tubing section 78, to be forced, under the suction exerted by the peristaltic pump roller 92, to the waste line 79, and then to the associated bag 100.

When the surgeon or operator desires to terminate aspiration quickly and to clean out entrapped material at the suction cannula, the VCS control is actuated. The pump 92 is shut off and concurrently the shunt actuator 96 is retracted. The slider bar 39 moves outwardly through the natural flexibility of the shunt tubing section 82 to allow a flow of sterile solution to reach the double-T fitting 74. At the same time, the irrigation actuator 94 forces the slider bar 38 down onto the irrigation tubing 58, closing off the irrigation flow. Suction on the aspiration line 72 is thus terminated and sterile solution flows through the shunt tubing section 82 into the double-T fitting 74. No impurities are introduced from the VCS fitting 98 because of the filter disk 88. When the irrigation/aspiration mode is resumed and the pump roller 92 is actuated the aspirated matter again passes out via the aspiration line 78 to the outlet fitting 81, the waste line 79, and the bag 100.

This arrangement is configured to use only relatively short lengths of tubing, and disposes the tubing principally in the side of the housing 12 adjacent the intercoupling edge. The system not only maintains the internal tubing sections filled for immediate switchover from the venting mode, but also has low priming volume. Furthermore, all internal contact with sterile tubing is made by sterile disposable elements. No matter how many times the slider bars 38, 39 are operated, which might tend to introduce a pinhole or fracture into one of the tubing sections, there is no danger of contamination from exterior sources under normal conditions, because of the sterility of the slider bars 38, 39 and cassette interior. No special mechanism is needed to maintain the sliders in position, because the normal resilience of the silicone-type tubing sections returns them to the non-pinching position as soon as the positive influence of the associated actuator is removed.

In addition, the operative tubing sections that are to be clamped are arranged in confined but controlled curvatures that do not tend to introduce kinking. Further, the end positions of most of the tubing are securely held, so that they are not misplaced or kinked even under rough handling. The short length of shunt tubing that is between the vent line path and the clamp does not pulse or resonate under substantial differential pressure in the irrigation/aspiration mode. This together with the firm securement of the other tubing sections improve the flow stability and smoothness of operation.

The slider bars 38, 30 block the adjacent apertures at the leading edge of the cassette 10, in effect providing a substantially closed configuration in this region. The projections 47 that contact the adjacent tubing sections can be shaped to provide best clamping action on the tubing section, while the opposed end can be given a curvature for contact with the associated actuator that provides best response and least wear. If, for operative reasons, the tubing sections are to be changed to different material or tubing which has a different clamping characteristic, the slider bar only need be changed to correspond.

Because all of the external tubing connections are made at the intercoupling side and via the stabilizer bar they are not only compactly arranged but firmly secured. Also, the arrangement includes attachment means for a separable waste bag. Thus if the surgical procedure is unexpectedly prolonged only the waste bag, and not the cassette itself, need be replaced.

While a number of forms and modifications in accordance with the invention have been described, it will be appreciated that the invention is not limited thereto but encompasses all modifications and expedients within the scope of the appended claims.

What is claimed is:

1. A cassette for sterile engagement with at least one tubing section to be clamped by an external actuator when the cassette is inserted into an associated mechanism, comprising:

a cassette housing having a first external edge for engagement proximate at least one actuator element when inserted in the mechanism;

means within the housing providing at least one backup surface proximate an external edge surface of the housing when the cassette is inserted;

means disposed at the external edge surface of the housing for coupling tubing in and out of the cassette, the tubing being arranged within the housing with at least one section adjacent the backup surface; and at least one slider element spanning from the first edge within the housing to at least one backup surface, to clamp the associated tubing section therebetween when the actuator element is operated within the mechanism.

2. The invention as set forth in claim 1 above, wherein the first edge of the cassette includes side wall means defining an access opening adjacent the at least one actuator element and the slider element being disposed therein between the side walls with a sliding fit.

3. The invention as set forth in claim 2 above, wherein the slider element is elongated along a first axis, and wherein the housing has a broad wall including a tongue along the first axis facing the slider element, and the slider element incorporates a groove mating with the tongue, to restrain movement of the slider element along the first axis.

4. The invention as set forth in claim 3 above, wherein the slider element includes an exterior face configured to receive the actuator element and an interior face edge comprising a projection for engagement against the associated tubing section, and wherein the tubing is silicone-type and the resilience of the tubing section is used to return the slider bar to position when the actuator is disengaged.

5. The invention as set forth in claim 4 above, wherein the housing comprises means defining two spaced apart backup surfaces, the system comprises two substantially like slider elements, and wherein the slider elements include side wings spaced apart from the exterior face and limiting outward movements of the slider elements by engagement against the side walls.

6. The invention as set forth in claim 5 above, wherein the cassette housing has a leading edge and the means defining access openings are disposed in the leading edge, and wherein the housing further includes an external edge on the side opposite the leading edge, at which the tube couplings are made.

7. The invention as set forth in claim 6 above, wherein the external edge of the housing comprises a stabilizer bar parallel to the leading edge, and open ended slots opposite sides of the housing for receiving the stabilizer bar, and wherein the cassette further comprises fittings mounted in the stabilizer bar for receiving matching ends of both external tubing and internal tubing.

8. A cassette for transporting both sterile irrigation and non-sterile aspiration fluids to or from a surgical handpiece in a system having a peristaltic aspiration pump, a shunt control element, a vacuum control system fitting and an irrigation control element disposed in linear fashion for accessibility to the leading edge of the cassette, comprising:

a housing for confining tubing sections in internal paths, the housing having a leading edge and an opposite intercoupling edge, and including tubing fittings for connections to and from a handpiece, from an irrigation fluid supply and to a waste bag along the intercoupling edge thereof;

the housing further comprising means defining principal interior tubing section paths adjacent the intercoupling edge, and guide means extending from adjacent the leading edge toward the intercoupling edge in alignment with the shunt control element and irrigation control element;

internal tubing sections disposed along the paths; and a pair of sliders engaging the guide means and movable inwardly under control of the control elements to clamp tubing sections therein.

9. A cassette as set forth in claim 8 above, wherein the housing includes a stabilizer bar along the intercoupling edge, and the tubing fittings are mounted in the stabilizer bar for coupling between the internal tubing sections and external tubing.

10. A cassette as set forth in claim 8 above, wherein the housing includes waste bag attachment means disposed along the intercoupling edge and the cassette further includes a waste bag for separable coupling to the attachment means.

11. A cassette as set forth in claim 8 above, wherein the cassette includes an internal line in communication with the vacuum control system fitting, and a shunt tubing section in communication with the internal line, the shunt tubing section being disposed in operative relation to the internal edge of the slider engaged by the shunt control element.

12. A cassette as set forth in claim 11 above, wherein the length of shunt tubing section between the region of engagement by the slider and the internal line is of the order of about one inch or less.

13. A cassette including internal flexible tubing to be selectively clamped by an external actuator, wherein at least a first internal tubing section intercouples elements or lines within the cassette, the combination comprising:

a cassette having an access opening along one edge for disposition adjacent the external actuator;

a first tubing section interior to the cassette;

fixed means adjacent the first tubing section on a side thereof opposite the access opening;

slider means adjacent the first tubing section on the opposite side thereof from the fixed means, the first tubing section being disposed opposite the cassette edge including the access opening, wherein the slider means is linearly movable between the cassette edge and the first tubing section, the slider means being movable by the external actuator between a rest position in which the first tubing section is not occluded and a blocking position in which the first tubing section id occluded by engagement against the fixed means;

a leading edge for insertion adjacent the external actuator, the slider means including an exposed end face for engagement by the external actuator and an end projection at the opposite end for engaging the first tubing section; and at least one additional access opening in the leading edge, at least a second tubing section and second fixed means, and at least a second slider means disposed between the additional access opening and the second tubing section.

* * * * *